(12) United States Patent
Ho (10) Patent No.: US 9,326,988 B2
(45) Date of Patent: May 3, 2016

(54) TREATMENT AND/OR PREVENTION OF PARKINSON'S DISEASE DEMENTIA WITH CEFTRIAXONE

(71) Applicants: CHUNG SHAN MEDICAL UNIVERSITY, Taichung (TW); TL & GM Chemical Company, Tainan (TW)

(72) Inventor: Ying-Jui Ho, Taichung (TW)

(73) Assignees: CHUNG SHAN MEDICAL UNIVERSITY, Taichung (TW); TL & GM CHEMICAL COMPANY, Tainan (TW)

( * ) Notice: Subject to any disclaimer, the term of this patent is extended or adjusted under 35 U.S.C. 154(b) by 82 days.

(21) Appl. No.: 13/801,480

(22) Filed: Mar. 13, 2013

(65) Prior Publication Data

US 2013/0296294 A1    Nov. 7, 2013

(30) Foreign Application Priority Data

May 1, 2012    (TW) .............................. 101115464 A (51) Int. Cl.
*A61K 31/546*    (2006.01)
(52) U.S. Cl.
CPC .................................... *A61K 31/546* (2013.01)
(58) Field of Classification Search
CPC .................................................... A61K 31/546
See application file for complete search history.

(56) References Cited

U.S. PATENT DOCUMENTS

2007/0238717 A1    10/2007    Rothstein et al.

FOREIGN PATENT DOCUMENTS

WO    WO2005/041978    *    5/2005
WO    WO 2005/041978 A1    5/2005

OTHER PUBLICATIONS

Leung et al. in Chemical Neuroscience 2012, 3, 22-30.*
Reagen-Shaw in FASEB Journal 22, 659-661 (2007).*
Lee et al. in Journal of Biological Chemistry 283(19), 13116-13122.*
Rumbaugh et al. in Journal of NeuroVirology (2007) 13, 168-172.*
Rabey et al. in J Neural Transm [P-D Sect] (1992) 4:277-282.*
Meurat Emre et al. in The Lancet.com/neurology vol. 9, 969-977 (2010).*
Christidi et al. in Cogn Behav Neurol 2014; 27:51-56.*
Nitrini, R. in Alzheimer Dis Assoc Disord 2005; 19:156-158.*
Parkinson's Disease Dementia in www.alz.org/dementia /parkinsons-disease-symptoms.asp (retrieved from the internet Mar. 9, 2016).*
Leung, Tch et al.; "Ceftriaxone ameliorates motor deficits and protects dopaminergic neurons in 6-hydroxydopamine-lesioned rats"; ACS Chemical Neuroscience, Jan. 18, 2012; pp. 22-30.
Christopher M. Lauderback et al., "The glial glutamate transporter, GLT-1, is oxidatively modified by 4-hydroxy-2-nonenal in the Alzheimer's disease brain: the role of A$\beta$1-42," Journal of Neurochemistry, Dec. 31, 2011, vol. 78: pp. 413-416.
CN Search Report dated Jun. 24, 2014 with English translation, pp. 1-6.
Mariateresa Buongiorno et al., "Amyloid-$\beta$ and $\tau$ biomarkers in Parkinson's disease-dementia," Journal of the Neurological Sciences, Jul. 20, 2011, vol. 310: pp. 25-30.

* cited by examiner

*Primary Examiner* — Dennis Heyer
(74) *Attorney, Agent, or Firm* — Birch, Stewart, Kolasch & Birch, LLP (57) ABSTRACT

Disclosed herein is a method for treatment of a human subject having or suspected of having Parkinson's disease dementia, which includes administering to the human subject ceftriaxone at a daily dosage ranging from about 1.5 mg to about 35 mg per kilogram of a body weight of the human subject.

7 Claims, 8 Drawing Sheets

TREATMENT AND/OR PREVENTION OF PARKINSON'S DISEASE DEMENTIA WITH CEFTRIAXONE

CROSS-REFERENCE TO RELATED APPLICATION

This application claims priority of Taiwanese Application No. 101115464, filed on May 1, 2012.

BACKGROUND OF THE INVENTION

1. Field of the Invention

This invention relates to the treatment and/or prevention of Parkinson's disease dementia (PDD) with ceftriaxone. A daily dosage of ceftriaxone for the treatment and/or prevention of PDD of a human subject according to this invention ranges from about 1.5 mg/kg to about 35 mg/kg.

2. Description of the Related Art

Dementia can be classified into the following two categories based on the part of the brain which is influenced: (1) cortical dementia, for example, Alzheimer's disease (AD), dementia with Lewy bodies (DLB), Frontal-temporal dementia (FTD), etc.; and (2) subcortical dementia, for instance, Parkinson's disease dementia (PDD), Huntington's disease (HD), etc.

Parkinson's disease (PD) is a common neurodegenerative disease, and the clinical symptoms thereof include resting tremor, rigidity, bradykinesia, and postural instability. The pathogenesis of PD might be related to degeneration of dopaminergic neurons in the substantia nigra pars compacta (SNc) and formation of Lewy bodies. Cardinal motor symptoms occur in patients with PD. In addition, about 25-50% of the aforesaid patients develop impairment of cognitive functions, which further leads to dementia (i.e. PDD). The impairment of cognitive functions regarding patients with PDD includes impairment in attention, working memory, executive functions, constructional abilities, and visuospatial functions.

The neuropsychological difference between patients with AD and PDD has been investigated in numerous studies, in particular, the difference in the impairment of cognitive functions. For instance, primacy of memory loss is a typical symptom of AD, but not a typical symptom of PDD. However, disturbances in attention, motivation, and access and manipulation of knowledge, and psychomotor slowing all are typical symptoms of PDD (Song I. U. et al. (2008), *Eur.Neurol.*, 59:49-54). Furthermore, a document has reported that: compared to patients with AD, the patients with PDD have instrumental functions (such as language and praxis) which are less impaired, verbal fluency and visuospatial functions (e.g., visual perception) which are more impaired, and hallucination which is more sever, and commonly suffer from personality change and depressive symptoms (Emre M. (2003), *Lancet Neurology*, 2:229-237).

The conventional drug commonly used clinically to treat PDD is rivastigmine (brand name Exelon®). However, rivastigmine is only able to cure mild or moderate PDD, and might cause symptoms of PD (in particular, tremor) to worsen. Moreover, the conventional drug Levodopa (L-dopa) commonly used clinically to ameliorate motor symptoms of PD has a limited therapeutic effect on impairment of cognitive functions (Emre M. (2003), supra). Therefore, it is inevitable to develop or find a drug that is capable of being effective in treating PDD.

Ceftriaxone is a broad-spectrum β-lactam antibiotic and is commonly used clinically to treat infections arising from Gram-positive and Gram-negative bacteria. In recent years, the treatment of neurodegenerative diseases (e.g., PD and dementia) with ceftriaxone has been noticed. For example, the doctoral dissertation completed by Leung Cheuk Hung in 2007 while attending Hong Kong Baptist University (name: Glutamate Antagonism as a Potential Treatment of Parkinson's Disease: A Study in a Rat Model) reports that ceftriaxone was applied to 6-hydroxydopamine (6-OHDA)-lesioned rats (an animal model of PD). The experimental results of the aforesaid dissertation indicates that ceftriaxone is useful in amelioration of motor symptoms and neuroprotection of dopaminergic neurons.

U.S. 2004/0191803 A1 discloses a method of treating impaired cognitive function in a mammal, which comprises the step of administering a therapeutically effective amount of ceftriaxone or an analog or derivative thereof to the aforesaid mammal. The aforementioned impaired cognitive function may be associated with the following diseases or disorders: mild cognitive impairment (MCI), age related cognitive decline (ARCD), memory loss, senility, and dementia (e.g., DLB, vascular dementia, AD, and HIV associated dementia). Particularly, in the examples of the aforesaid prior art document, aged-impaired (AI) rats were treated with ceftriaxone at a daily dose of 200 mg/kg for 7 days. The experimental result shows that ceftriaxone is able to ameliorate cognitive impairment of the AI rats.

In Hota S. K. et al. (2008), *Neurobiology of Learning and Memory*, 89:522-532, rats chronically exposed to hypobaric hypoxia were treated with ceftriaxone. The experimental result reveals that ceftriaxone is capable of ameliorating the cognitive impairment resulting from hypobaric hypoxia, reducing oxidative stress in the hippocampus, and decreasing neuronal degeneration and chromatin condensation. Consequently, ceftriaxone is expected to be useful for treating AD and ischemic and hypoxic conditions that are associated with excitotoxicity.

As far as the inventor is aware, so far, there have been no documents or prior art patents which disclose that ceftriaxone can be utilized in the treatment of PDD. Through research, the inventor has found that cognitive functions (such as working memory and recognition ability) of rats having PDD can be ameliorated by administering ceftriaxone at a daily dosage ranging from 10 to 200 mg/kg. Accordingly, the inventor deduces that ceftriaxone is useful in the treatment and/or prevention of PDD in a human subject at a specific dosage.

SUMMARY OF THE INVENTION

According to this invention, a method for treating a human subject having or suspected of having Parkinson's disease dementia includes administering to the human subject ceftriaxone at a daily dosage ranging from about 1.5 mg to about 35 mg per kilogram of a body weight of the human subject.

BRIEF DESCRIPTION OF THE DRAWINGS

The above and other objects, features and advantages of this invention will become apparent with reference to the following detailed description and the preferred embodiments taken in conjunction with the accompanying drawings, in which:

FIG. 3 shows the correct response rate of rats in each group as determined via a T-maze test, in which the symbol "***"

represents p<0.001 when the respective group is compared with the sham-operated group 1; the symbol "#" represents p<0.05 when the respective group is compared with the pathological control group; and the symbol "##" represents p<0.01 when the respective group is compared with the pathological control group;

DETAILED DESCRIPTION OF THE PREFERRED EMBODIMENTS

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which this invention belongs. One skilled in the art will recognize many methods and materials similar or equivalent to those described herein, which could be used in the practice of this invention. Indeed, this invention is in no way limited to the methods and materials described. For clarity, the following definitions are used herein.

As used herein, the term "treating" or "treatment" refers to reducing, alleviating, ameliorating, relieving, or controlling one or more clinical signs of a disease or disorder, and lowering, stopping, or reversing the progression of severity regarding the condition or symptom being treated.

As used herein, the term "Parkinson's disease dementia (PDD)" refers to dementia that a patient having Parkinson's disease develops. Symptoms of PDD include the following impairment of cognitive functions: impairment in attention, working memory, short-term memory, executive functions, recognition abilities, constructional abilities, visuospatial functions, and verbal fluency.

When developing a drug that can be used in the treatment and/or prevention of PDD, the inventor found that ceftriaxone is suitable to treat and/or prevent PDD. The inventor also found that ceftriaxone is effective in treatment of neuron inflammation and prevention of neuron degeneration in a subject suffered from PDD.

Therefore, the inventor deems that ceftriaxone can be used to prepare a drug for treating and/or preventing PDD in a human subject.

In particular, by virtue of the experimental results, the inventor proved that: when ceftriaxone is administered to rats with PDD at a daily dosage ranging from 10 to 200 mg/kg, cognitive functions (such as working memory and recognition ability) of the aforementioned rats can be effectively ameliorated. The aforesaid dosage range suitable for rats can be converted to a dosage range suitable for human or other animals according to the formula for dose translation based on BSA (body surface area), which is described in Shannon R. S. et al. (2007), *FASEB J.*, 22:659-661.

Accordingly, this invention provides a method for treating a human subject having or suspected of having Parkinson's disease dementia, which comprises administering to the human subject ceftriaxone at a daily dosage ranging from about 1.5 mg to about 35 mg per kilogram of a body weight of the human subject.

In a preferred embodiment of this invention, the dosage of ceftriaxone ranges from about 1.62 mg to about 32.4 mg; more preferably, from 1.62 mg to about 16.2 mg; most preferably, from about 1.62 mg to about 8.1 mg, per kilogram of the body weight of the human subject.

Preferably, ceftriaxone is formulated into a pharmaceutical composition and with a suitable dosage form for parenteral or oral administration using technology well known to those skilled in the art. The suitable dosage form includes, but is not limited to, injections (e.g., sterile aqueous solutions or dispersions), sterile powder, tablets, troches, lozenges, pills, capsules, dispersible powder or granules, solutions, suspensions, emulsions, syrups, elixirs, slurries, and the like.

The pharmaceutical composition according to this invention may be administered via one of the following parenteral routes: intraperitoneal injection, intrapleural injection, intramuscular injection, intravenous injection, intraarterial injection, intraarticular injection, intrasynovial injection, intrathecal injection, intracranial injection, and sublingual administration.

In a preferred embodiment of this invention, the pharmaceutical composition is formulated into a suitable dosage form for intraperitoneal injection.

The pharmaceutical composition according to this invention can additionally comprise a pharmaceutically acceptable carrier widely employed in the art of drug-manufacturing. For instance, the pharmaceutically acceptable carrier may include one or more of the following agents: solvents, emulsifiers, suspending agents, decomposers, binding agents, excipients, stabilizing agents, chelating agents, diluents, gelling agents, preservatives, lubricants, absorption delaying agents, liposomes, and the like.

The choice and amount of the aforesaid agents are within the expertise and the routine skills of those skilled in the art.

According to this invention, the pharmaceutically acceptable carrier may include one of the following solvents: water, normal saline, phosphate buffered saline (PBS), sugar-containing solutions, aqueous solutions containing alcohol, and combinations thereof.

The dosage and the frequency of administration of the pharmaceutical composition according to this invention may vary depending on the following factors: the severity of the disease to be treated, the route of administration, and the age, physical condition and response of the subject to be treated. Generally speaking, the pharmaceutical composition according to this invention may be administered orally or parenterally in a single dose or in several doses.

This invention will be further described by way of the following examples. However, it should be understood that the following examples are solely intended for the purpose of illustration and should not be construed as limiting the invention in practice.

EXAMPLES

Experimental Materials:
1. Experimental Animals:

The male Wistar rats (12 weeks of age, a body weight of about 419.5±7.5 g) used in the examples below were purchased from National Laboratory Animal Center (R.O.C.). All of the experimental animals were respectively kept in transparent cages under the following laboratory conditions: temperature of 24±1° C., relative humidity of 60±5%, and a 12 hour light/12 hour dark cycle (lights on at 7:00 am). Furthermore, water and food were provided ad libitum.

Figure 1:
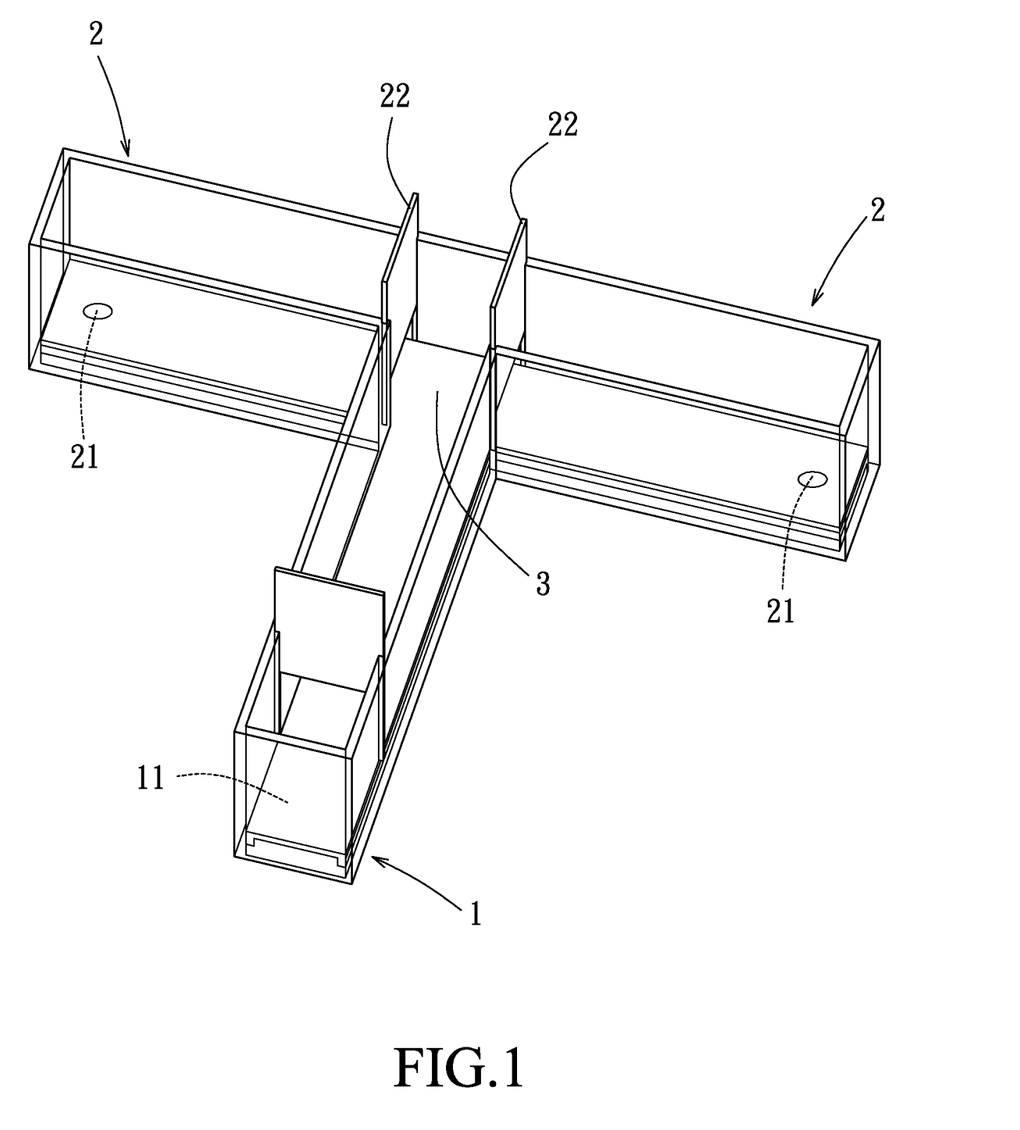
FIG. 1 is a perspective view of a T-maze.

From the second day to the fourth day of being kept, each of the animals was handled for 5 minutes per day so as to reduce stress responses thereof to an experimenter and an experimental environment. All experimental procedures involving the experimental animals were approved by Animal Care Committee of Chung Shan Medical University and were performed in accordance with the NIH (National Institutes of Health) Guide for the Care and Use of Laboratory Animals.
2. T-Maze:

The T-maze used in the examples below is shown in FIG. 1. The T-maze was made of black polyvinyl plastics, was generally in the shape of the letter "T", and was composed of a start arm 1 (60 cm long×15 cm wide×30 cm high), two opposed choice arms 2 (40 cm long×10 cm wide×30 cm high), and a central square 3 (15 cm long×10 cm wide×30 cm high) interconnecting the start arm 1 and the choice arms 2. The start arm 1 has a start end 11 opposite to the central square 3. Each of the choice arms 2 has a terminal end 21 opposite to the central square 3.

In addition, each of the choice arms 2 has a sliding door 22. When the sliding door 22 of one of the choice arms 2 was closed, the respective experimental animal can move from the start end 11 to the terminal end 21 of the other one of the choice arm 2 through the sliding door 22 thereof, which was opened. Moreover, the sliding doors 22 of both of the choice arms 2 could be simultaneously opened so that the respective experimental animal was allowed to move from the start end 11 to the terminal end 21 of any one of the choice arms 2 through the sliding door 22 thereof.

Figure 2A:
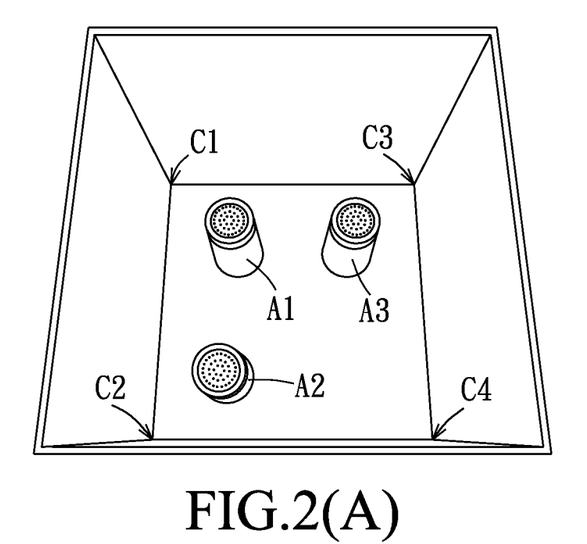
FIG. 2(A) is a top view to illustrate an open box and three objects A1, A2, A3 disposed therein.
Figure 2B:
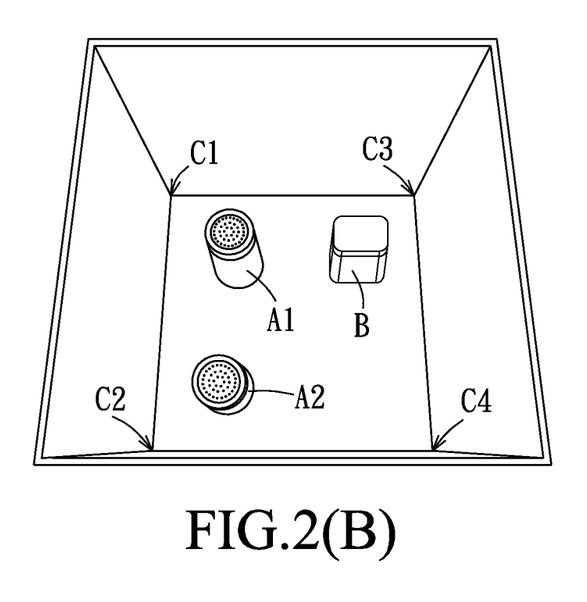
FIG. 2(B) is a top view illustrating that the object A3 in the open box as shown in FIG. 2(A) is replaced with an object B.

The T-maze was thoroughly cleaned using 20% ethanol and was subsequently thoroughly dried before each of the experimental animals was tested.
3. Open Box:

The open box used in the examples below (60 cm long×60 cm wide×60 cm high) is shown in FIGS. 2(A) and 2(B). The open box was made of black polyvinyl plastics. Three objects, which were respectively designated as A1, A2, and A3, were identical in terms of size, color, shape, and material, and had no specific scents. Each of the objects A1, A2, A3 was placed on the bottom of the open box and was spaced apart from a respective one of three corners C1, C2, C3 of the open box by 27 cm (see FIG. 2(A)). The object A3 was later replaced with an object B different from the object A3 in terms of size, color, shape, and material, and having no specific scents (see FIG. 2(B)). Prior to an experiment, each of the objects A1, A2, A3, B was unfamiliar to the experimental animals. The open box and the objects A1, A2, A3, B were thoroughly cleaned using 20% ethanol, and were subsequently thoroughly dried before each of the experimental animals was tested.

Example 1

Evaluation for Therapeutic Effect of Ceftriaxone on Rats with Parkinson's Disease Dementia (PDD)

1-methyl-4-phenyl-1,2,3,6-tetrahydropyridine hydrochloride (MTPT-HCl) was used to induce PDD in the rats, and the therapeutic effect of ceftriaxone on PDD was evaluated via behavioral tests and histopathological assessment of the brain for the rats. The experiments of this example were conducted substantially according to the method as described in Ho Y. J. et al. (2011), *Behav. Brain Res.*, 219:280-290.
Experimental Procedures:
A. Induction of PDD The male Wistar rats were randomly divided into the following groups: a pathological control group (n=48), two preventive groups (i.e. preventive group 1 (n=12) and preventive group 2 (n=12)), three treatment groups (i.e. treatment group 1 (n=15), treatment group 2 (n=12), and treatment group 3 (n=12)), and three sham-operated groups (i.e. sham-operated group 1 (n=38), sham-operated group 2 (n=7), and sham-operated group 3 (n=8)).

The rats in the pathological control group, the preventive groups, and the treatment groups were anesthetized using Zoletil (Virbac, Carros, France; 20 mg/kg, intraperitoneal injection). Afterward, 0.5 M MPTP-HCl (in saline) was slowly infused bilaterally into the substantia nigra pars compacta (SNc) of the mesencephalon of each rat in the pathological control group, the preventive groups, and the treatment groups (0.21 mg/side) so as to induce the same to develop PDD.

The rats in the sham-operated groups were generally subjected to the same surgical procedures for the rats in the pathological control group, the preventive groups, and the treatment groups, except that an equal volume of saline was infused bilaterally into the SNc of the mesencephalon of rats in the shame-operated groups.

Penicillin-G procaine was immediately injected into each of the rats in each group (0.2 mL, 20,000 IU) so as to prevent post-operative infection. The rats in each group were housed individually in plastic cages, and the wounds thereof were allowed to heal for about 7 days. Subsequently, the rats in each group were transferred to the home cages.

B. Administration of Ceftriaxone 5 days before the MPTP-HCl injection, ceftriaxone (Sigma) was administered to the rats in the preventive groups 1,2 via intraperitoneal injection respectively at a daily dose of 100 mg/kg and at a daily dose of 200 mg/kg until the end of the 14$^{th}$ day after the MPTP-HCl injection. After the MPTP-HCl injection, ceftriaxone was administered to the rats in the treatment group 1 and the sham-operated groups 2,3 via intraperitoneal injection respectively at a daily dose of 200 mg/kg, at a daily dose of 100 mg/kg, and at a daily dose of 200 mg/kg, and saline was administered to the rats in the pathological control group and the sham-operated group 1 via intraperitoneal injection at a daily dose of 1 mL/kg. In addition, starting on the 3$^{rd}$ day after the MPTP-HCl injection, ceftriaxone was administered to the rats in the treatment groups 2,3 via intraperitoneal injection respectively at a daily dose of 100 mg/kg and at a daily dose of 200 mg/kg. The rats in the pathological control group, the treatment groups 1,2,3, and the sham-operated groups 1,2,3 were subjected to the once-a-day administration until the end of the 14$^{th}$ day after the MPTP-HCl injection.

Starting on the 8$^{th}$ day after the MPTP-HCl injection, the rats in each group were subjected to the T-maze test as described in section C of this example. Starting on the 12$^{th}$ day after the MPTP-HCl injection, the rats in each group were subjected to the object recognition test as described in section D of this example. On the 15$^{th}$ day after the MPTP-HCl injection, the rats in the treatment group 1, the sham-operated group 1, and the pathological control group were subjected to the histopathological analysis as described in section E of this example.

C. T-Maze Test

In order to investigate the effect of ceftriaxone on the working memory of the rats with PDD, on the 8$^{th}$ day after the MPTP-HCl injection, 11 rats, 32 rats, and 36 rats were randomly selected respectively from the treatment group 1, the sham-operated group 1, and the pathological control group, and the aforesaid randomly selected rats and each of the rats in the rest of the groups were subjected to a T-maze test. The T-maze test lasted a total of three days, and was conducted substantially according to the following methods:

(1) One day before the start of the T-maze test, the rats are subjected to 23 hours of fasting. Furthermore, on each of three days for the training session, after all of trials were finished, the rats were fed for an hour.

(2) The training session—the 1$^{st}$ and 2$^{nd}$ days of the T-maze test:

The respective rat is subjected to a total of 9 trials. In each of the trials, one forced run and one choice run were sequentially conducted. The time interval between the forced run and the choice run was 30 seconds. The respective rat was placed at the start end 11 of the T-maze to begin either the forced run or the choice run. When the forced run was conducted, the sliding door 22 of one of the two choice arms 2 was closed, and a food serving as a reward was placed at the terminal end 21 of the other one of the two choice arms 2. Once the respective rat gets the reward, the forced run was considered finished. When the choice run was conducted, the sliding doors 22 of both of the two choice arms 2 were opened. A food serving as a reward was placed at the terminal end 21 of the choice arm 2 which had the sliding door 22 in a closed state during the previously conducted forced run (but now having the sliding door 22 in an open state). When the respective rat entered either one of the two choice arms 2, the choice run is considered finished. During the choice run, the respective rat was considered as making a correct response when the same entered the choice arm 2 which had the sliding door 22 in a closed state during the previously conducted forced run (but now having the sliding door 22 in an open state).

(3) The Test Session—The 3$^{rd}$ Day of the T-Maze Test:

The respective rat was subjected to a total of 3 trials. In each of the trials, one forced run and two consecutive choice runs were sequentially conducted. The respective rat was placed at the start end 11 of the T-maze to begin either the forced run or the choice run. The number of correct responses made by the respective rat during the 6 choice runs in total was recorded.

The working memory of the respective rat was evaluated based on the correct response rate as calculated from the results obtained in the test session (i.e. the 3$^{rd}$ day of the T-maze test or the 10$^{th}$ day after the MPTP-HCl injection). The correct response rate can be calculated by substituting the number of correct responses obtained in the test session into the following formula:

$$A = (B/6) \times 100 \tag{1}$$

where A=the correct response rate (%)

B=the number of correct responses

The experimental data are expressed as mean±SEM. The experimental data were subjected to one-way analysis of variance (ANOVA) and were subsequently subjected to least-significant difference (LSD) test such that the difference between the sham-operated group 1 and a respective one of the sham-operated groups 2, 3, the difference between the pathological control group and the sham-operated group 1, and the difference between the pathological control group and a respective one of the treatment groups 1, 2, 3 and the preventive groups 1,2 could be evaluated. Statistical significance is indicated by p<0.05.

D. Object Recognition Test

In order to examine the effect of ceftriaxone on the recognition and/or memory ability of the rats with PDD, starting on the 12$^{th}$ day after the MPTP-HCl injection, all of the rats in each group were subjected to an object recognition test lasting a total of three days.

The object recognition test is described as follows. The object recognition test included four trials. The first and second trilas were conducted respectively on the 12$^{th}$ and 13$^{th}$ after the MPTP-HCl injection, and the third and fourth trials were conducted on the 14$^{th}$ day after the MPTP-HCl injection. Each of the four trials lasted 5 minutes. The time interval between the first and second trials, and that between the second and third trials were 1 day. The time interval between the third and fourth trials was 5 minutes. At the beginning of each of the four trials, the respective rat was placed in the open box and adjacent to the corner C4 thereof. During the first, second, and third trials, the objects A1, A2, A3 were disposed in the open box for being able to be explored by the respective rat (see FIG. 2(A)). During the fourth trial, the object A3 was replaced with the object B (see FIG. 2(B)). During the object recognition test, a video camera installed above the open box was used to monitor and record the behavior of the respective rat. By virtue of the video camera, the time spent by the respective rat exploring an object (i.e. the object A1, A2, A3, or B) during a trial (i.e. the first, second, third, or fourth trial) was measured. Exploration of an object is defined as approaching the object and physically contacting the object with a snout and/or a forepaw. The time spent by the respective rat exploring an object in a trial is referred to as exploration time spent on an object in a trial. The difference between the percentage of exploration time spent on the object A3 in the third trial and the percentage of exploration time spent on the object B in the fourth trial can be used as an index for evaluating the ability to memorize a familiar object, and the ability to recognize the dissimilarity between the familiar object and a novel object. The percentage of exploration time spent on the object A3 in the third trial and the percentage of exploration time spent on the object B in the fourth trial can be calculated using the following formula:

$$C=(D/E)\times 100 \qquad (2)$$

where C=the percentage of exploration time spent on the object A3 in the third trial or the percentage of exploration time spent on the object B in the fourth trial (%)
D=exploration time spent on the object A3 in the third trial or exploration time spent on the object B in the fourth trial
E=total exploration time spent on the objects A1,A2,A3 in the third trial or total exploration time spent on the objects A1,A2,B in the fourth trial The experimental data are expressed as mean±SEM. The experimental data were analyzed using paired-samples t-tests so as to evaluate the difference between the percentage of exploration time spent on the object A3 in the third trial and the percentage of exploration time spent on the object B in the fourth trial regarding the rats in the respective group. Statistical significance is indicated by $p<0.05$.

E. Histopathological Analysis

In order to investigate whether ceftriaxone is effective in ameliorating neuroinflammation and neurodegeneration of the rats with PDD, on the $15^{th}$ day after the MPTP-HCl injection, four rats were randomly selected from each of the treatment group 1, the sham-operated group 1, and the pathological control group for histopathological analysis.

The randomly selected rats were sacrificed using $CO_2$, followed by perfusion with 4% paraformaldehyde (in phosphate buffered saline). The brains were rapidly removed and were post-fixed in a 30% sucrose solution containing 4% paraformaldehyde at 4° C. for at least three days. The brains were cut into coronal sections (a thickness of about 30 μm) using a cryostat (Leica CM3050 S, Leica).

The sections containing SNc were selected. Subsequently, the selected sections were subjected to immunohistochemical staining using an anti-MHC class II antibody (OX-6; BD Biosciences Pharmingen, CA) as a primary antibody and a biotinylated horse anti-mouse IgG antibody (Vector Laboratory, CA) as a secondary antibody according to the method well known to and commonly used by one skilled in the art. The stained sections were observed at 200× magnification using an optical microscope (AXioskop2, ZEISS). Image Pro Plus Software 6.0 (Media Cybernetics) was utilized to determine the density of activated microglia in an area of 18,769 μm².

In addition, the sections containing the hippocampal CA1 area were selected and were subjected to Nissl staining according to the method well known to and commonly used by one skilled in the art. The stained sections were observed at 200× magnification using an optical microscope (AXioskop2, ZEISS). Image Pro Plus Software 6.0 was utilized to estimate the percentage of an area occupied by pyramidal neurons in an area of 2,354 μm² according to the semi-quantitative method as described in Xavier L. L. et al. (2005), *Brain Research protocols,* 16:58-64.

The experimental data are expressed as mean±SEM. The experimental data were subjected to one-way ANOVA and were subsequently subjected to LSD test such that the difference between the pathological control group and the sham-operated group 1, and the difference between the treatment group 1 and the pathological control group could be evaluated. Statistical significance is indicated by $p<0.05$.

Results:

T-Maze Test

Figure 3:
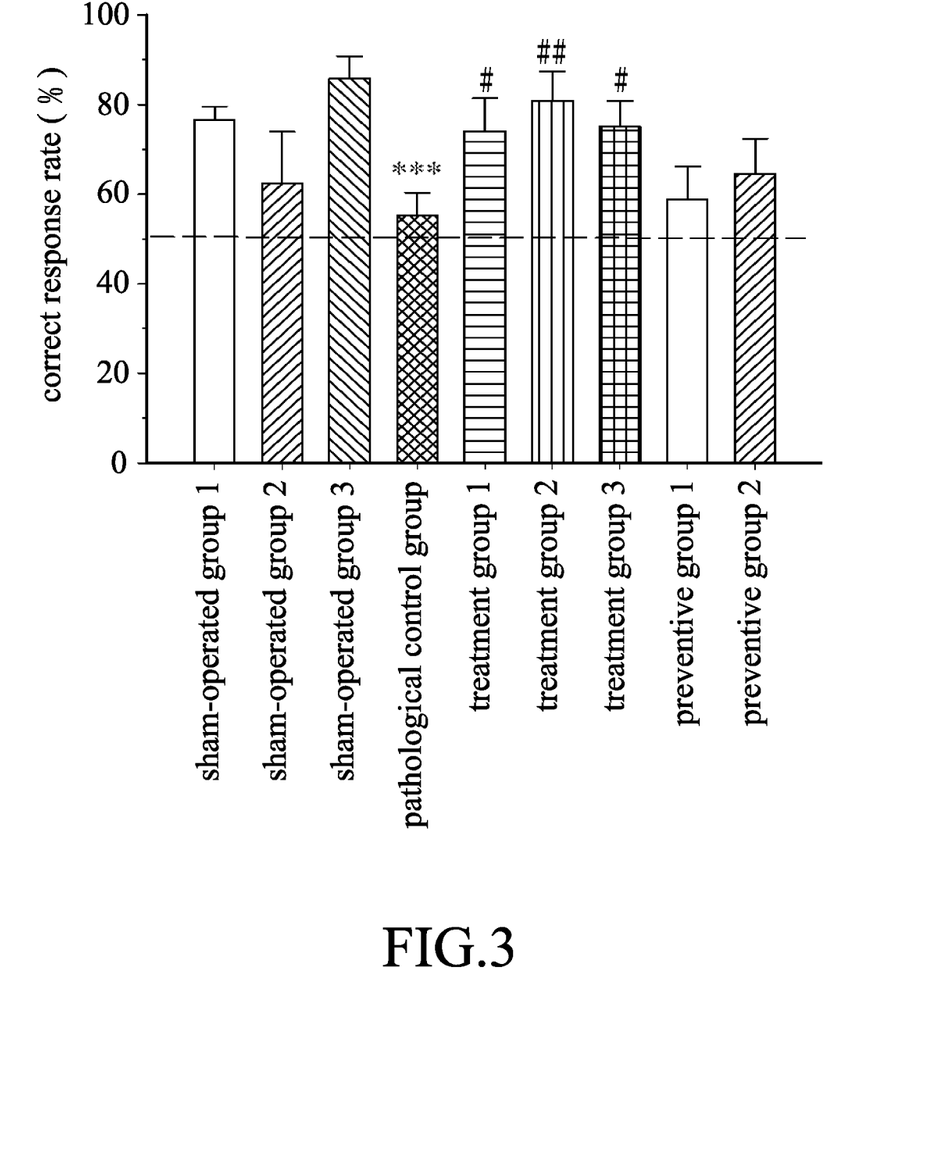

FIG. 3 shows the correct response rate of the rats in each group as determined via the T-maze test. Specifically speaking, the correct response rate of the rats in each group was determined on the $10^{th}$ day after the MPTP-HCl injection (i.e. the last day of the T-maze test). As shown in FIG. 3, there is no statistical significance between the correct response rate of the rats in the sham-operated group 1 and that of the rats in a respective one of the sham-operated groups 2, 3, thereby indicating that ceftriaxone does not negatively affect working memory of normal rats. Compared to the rats in the sham-operated group 1, the correct response rate of the rats in the pathological control group is significantly lower, thereby revealing that MPTP-HCl successfully induces rats to develop PDD and causes the same to have a defect in working memory. Compared to the rats in the pathological control group, the correct response rate of the rats in the treatment groups 1, 2, 3 and the preventive groups 1, 2 is higher. Particularly, there is statistical significance between the correct response rate of the rats in the pathological control group and that of the rats in a respective one of the treatment groups 1, 2, 3. The correct response rate of the rats in the treatment groups 1, 2, 3 is even close to that of the rats in the sham-operated group 1. The aforesaid experimental results show that ceftriaxone is effective in treating PDD and is able to ameliorate the working memory of the rats with PDD.

Object Recognition Test

Figure 4:
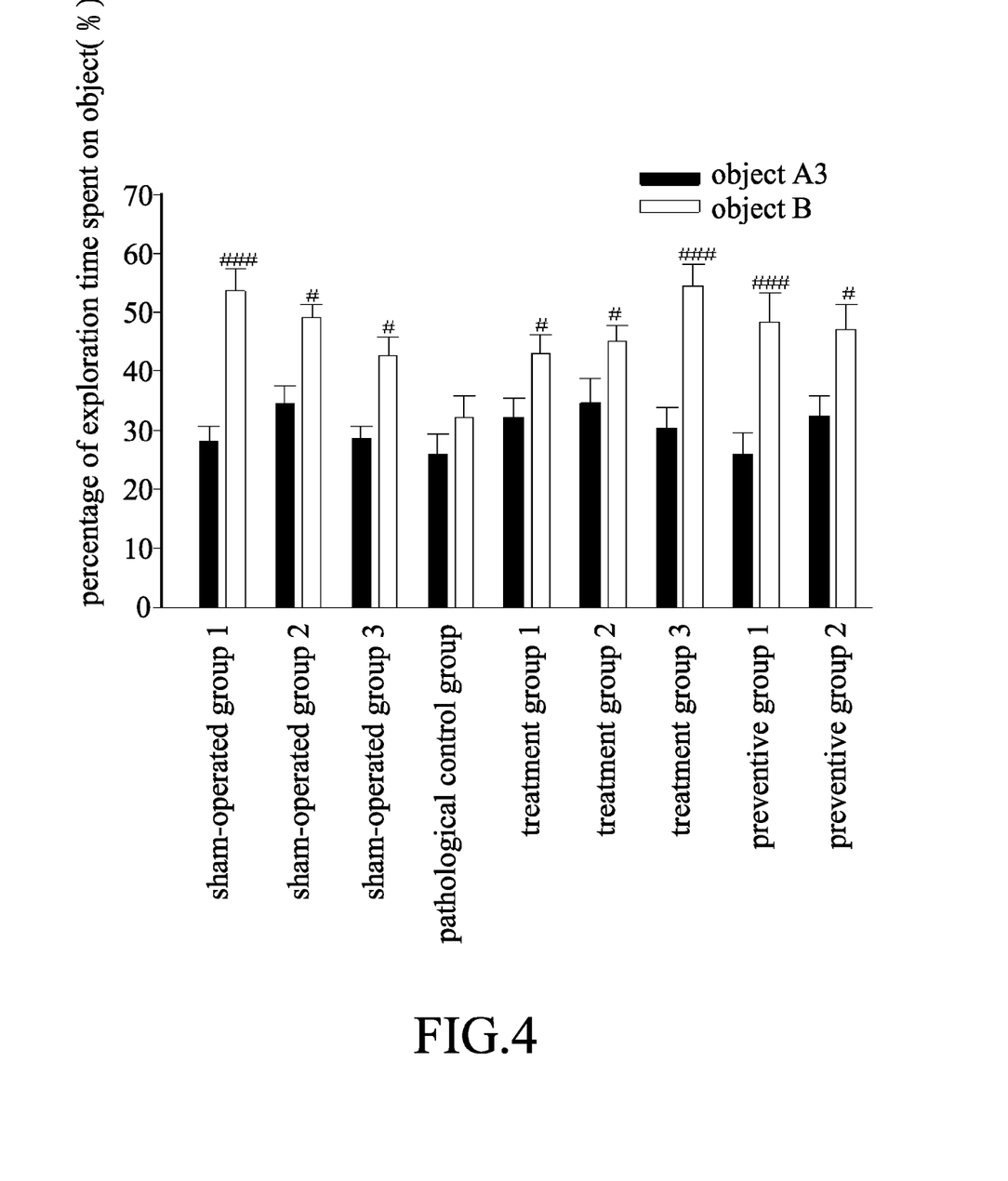
FIG. 4 shows the percentage of exploration time spent on an object A3 in a third trial and the percentage of exploration time spent on an object B in a fourth trial regarding rats in each group as determined via an object recognition test, in which the symbol "#" represents p<0.05 when the percentage of exploration time spent on the object A3 in the third trial and the percentage of exploration time spent on the object B in the fourth trial regarding the respective group are compared; and the symbol "###" represents p<0.001 when the percentage of exploration time spent on the object A3 in the third trial and the percentage of exploration time spent on the object B in the fourth trial regarding the respective group are compared.

FIG. 4 shows the percentage of exploration time spent on the object A3 in the third trial and the percentage of exploration time spent on the object B in the fourth trial regarding the rats in each group as determined via the object recognition test. Specifically speaking, the percentage of exploration time spent on the object A3 in the third trial and the percentage of exploration time spent on the object B in the fourth trial regarding the rats in each group were determined on the $14^{th}$ day after the MPTP-HCl injection (i.e. the last day of the object recognition test). As shown in FIG. 4, considering the rats in the sham-operated groups 1,2,3, there is statistical significance between the percentage of exploration time spent on the object B in the fourth trial and the percentage of exploration time spent on the object A3 in the third trial, thereby indicating that ceftriaxone does not negatively affect recognition and/or memory ability of normal rats. Considering the rats in the pathological control group, there is no statistical significance between the percentage of exploration time spent on the object B in the fourth trial and the percentage of exploration time spent on the object A3 in the third trial, thereby revealing that MPTP-HCl successfully induces rats to contract PDD and causes the same to have a defect in recognition and/or memory ability. On the contrary, considering the rats in the treatment groups 1, 2, 3 and the preventive groups 1, 2, there is statistical significance between the percentage of exploration time spent on the object B in the fourth trial and the percentage of exploration time spent on the object A3 in the third trial. The aforementioned experimental results show that ceftriaxone is able to prevent PDD, and to improve the ability to memorize a familiar object, and the ability to recognize a difference between the familiar object and a novel object, for the rats with PDD.

Histopathological Analysis

Figure 5:
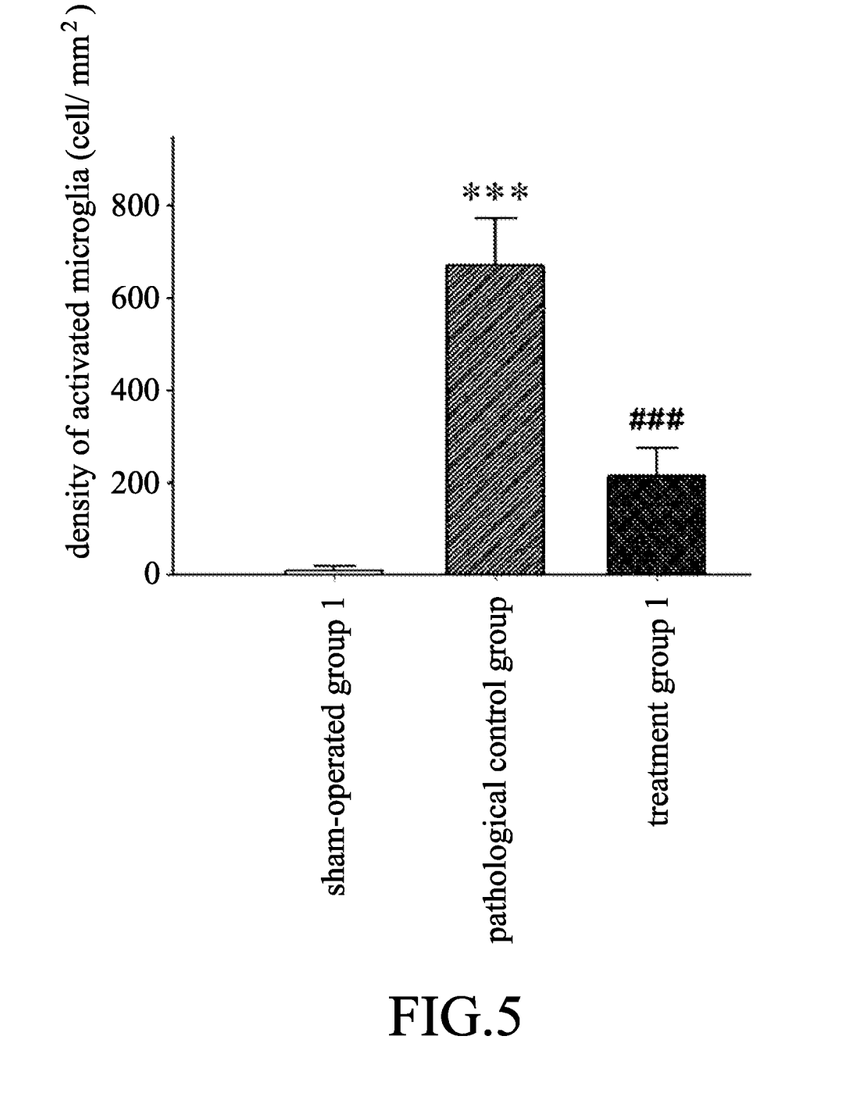
FIG. 5 shows the density of activated microglia in the SNc regarding rats in each group as determined via immunohistochemical staining, in which the symbol "***" represents p<0.001 when the respective group is compared with the sham-operated group 1; and the symbol "###" represents p<0.001 when the respective group is compared with the pathological control group.

FIG. 5 shows the density of activated microglia in the SNc regarding the rats in each group as determined via immunohistochemical staining. Specifically speaking, the density of activated microglia in the SNc regarding the rats in each group was determined on the 15$^{th}$ day after the MPTP-HCl injection. As shown in FIG. 5, compared to the rats in the sham-operated group 1, the density of activated microglia in the SNc regarding the rats in the pathological control group is significantly higher, thereby indicating that MPTP-HCl successfully induces rats to develop PDD, and results in the activation of microglia and the neuroinflammation thereof. Compared to the rats in the pathological control group, the density of activated microglia in the SNc regarding the rats in the treatment group 1 is significantly lower. The aforesaid experimental results show that ceftriaxone is effective in inhibiting the activation of microglia and the neuroinflammation regarding the rats with PDD.

Figure 6:
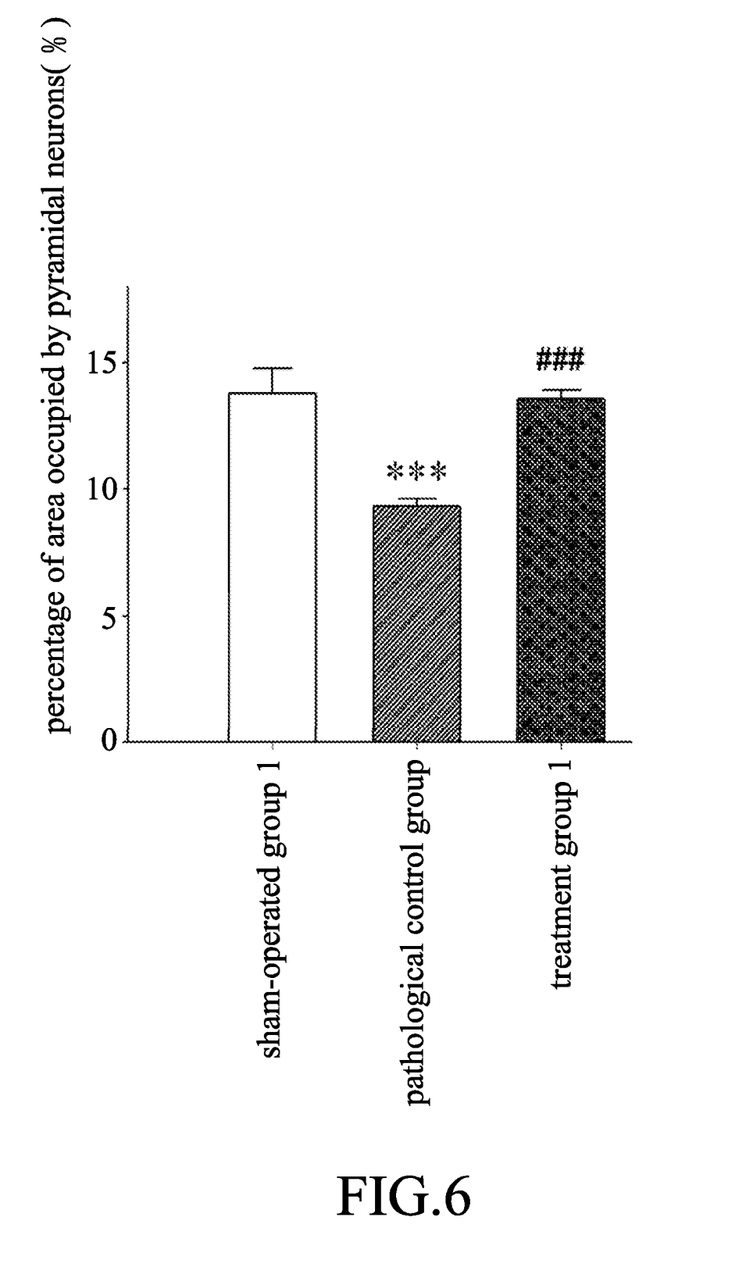
FIG. 6 shows the percentage of an area occupied by pyramidal neurons in the hippocampal CA1 area regarding rats in each group as determined via Nissl staining, in which the symbol "***"0 represents p<0.001 when the respective group is compared with the sham-operated group 1; and the symbol "###" represents p<0.001 when the respective group is compared with the pathological control group.

FIG. 6 shows the percentage of an area occupied by pyramidal neurons in the hippocampal CA1 area regarding the rats in each group as determined via Nissl staining. Specifically speaking, the percentage of an area occupied by pyramidal neurons in the hippocampal CA1 area regarding the rats in each group was determined on the 15$^{th}$ day after the MPTP-HCl injection. As shown in FIG. 6, compared to the rats in the sham-operated group 1, the percentage of an area occupied by pyramidal neurons in the hippocampal CA1 area regarding the rats in the pathological control group is significantly lower, thereby indicating that MPTP-HCl successfully induces rats to contract PDD and results in the hippocampal neurodegeneration thereof. Compared to the rats in the pathological control group, the percentage of an area occupied by pyramidal neurons in the hippocampal CA1 area regarding the rats in the treatment group 1 is significantly higher. The aforementioned experimental results show that ceftriaxone is effective in ameliorating the hippocampal neurodegeneration of the rats with PDD.

In view of the foregoing results of Example 1, the inventor deems that ceftriaxone is effective in preventing and treating PDD.

Example 2

Evaluation for Therapeutic Effect on Rats with PDD Regarding Low Dosage of Ceftriaxone In order to further examine whether a low dosage of ceftriaxone is also effective in treating PDD, the experiments of this example were conducted.

Experimental Procedures:

The male Wistar rats were randomly divided into the following groups: a pathological control group (n=23), two treatment groups (i.e. treatment group 1 (n=15) and treatment group 2 (n=13)), and a sham-operated group (n=27). The rats in each group were induced to contract PDD substantially according to the method as described in the section, entitled "A. Induction of PDD", of the Experimental Procedures in Example 1.

After the MPTP-HCl injection, ceftriaxone was administered to the rats in the treatment groups 1, 2 via intraperitoneal injection respectively at a daily dose of 10 mg/kg and at a daily dose of 50 mg/kg, and saline was administered to the rats in the pathological control group and the sham-operated group via intraperitoneal injection at a daily dose of 1 mL/kg. The rats in each group were subjected to the once-a-day administration until the end of the 14$^{th}$ day after the MPTP-HCl injection.

On the 8$^{th}$ day after the MPTP-HCl injection, 12 rats and 19 rats were randomly selected respectively from the treatment group 2 and the pathological control group, and the aforesaid randomly selected rats and each of the rats in the rest of the groups were subjected to a T-maze test substantially according to the method as described in the section, entitled "C. T-maze test", of the Experimental Procedures in Example 1. The correct response rate of the rats in each group was determined so as to evaluate the difference between the pathological control group and the sham-operated group, and the difference between the pathological control group and a respective one of the treatment groups 1, 2.

On the 12$^{th}$ day after the MPTP-HCl injection, 23 rats were randomly selected from the sham-operated group, and the aforesaid randomly selected rats and each of the rats in the rest of the groups were subjected to an object recognition test substantially according to the method as described in the section, entitled "D. Object recognition test", of the Experimental Procedures in Example 1. Therefore, the difference between the percentage of exploration time spent on the object A3 in the third trial and the percentage of exploration time spent on the object B in the fourth trial regarding the rats in the respective group could be evaluated.

Results:

T-Maze Test

Figure 7:
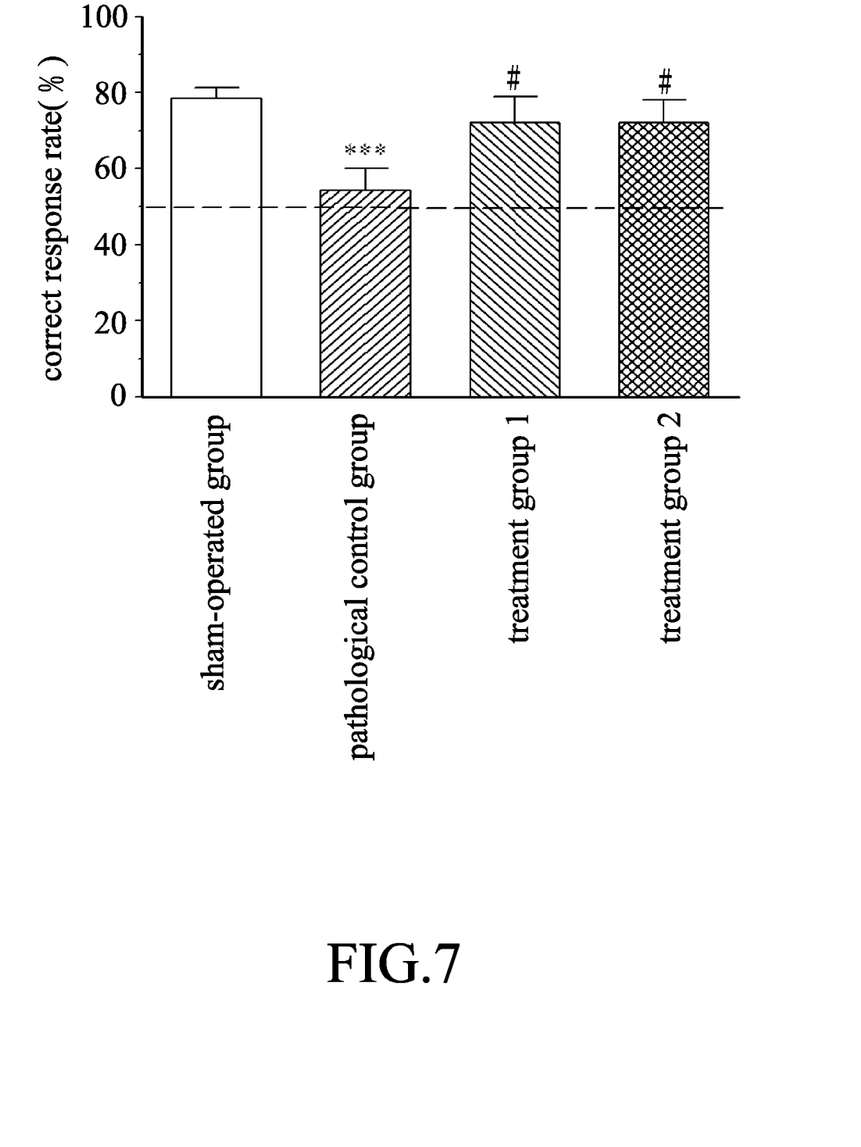
FIG. 7 shows the correct response rate of rats in each group as determined via a T-maze test, in which the symbol "***" represents p<0.001 when the respective group is compared with the sham-operated group; and the symbol "#" represents p<0.05 when the respective group is compared with the pathological control group.

FIG. 7 shows the correct response rate of the rats in each group as determined via the T-maze test. Specifically speaking, the correct response rate of the rats in each group was determined on the 10$^{th}$ day after the MPTP-HCl injection (i.e. the last day of the T-maze test). As shown in FIG. 7, compared to the rats in the sham-operated group, the correct response rate of the rats in the pathological control group is significantly lower. Compared to the rats in the pathological control group, the correct response rate of the rats in the treatment groups 1, 2 is significantly higher. The correct response rate of the rats in the treatment groups 1, 2 is even close to that of the rats in the sham-operated group. The aforesaid experimental results indicate that a low dosage of ceftriaxone is effective in treating PDD and is able to ameliorate the working memory of the rats with PDD.

Object Recognition Test

Figure 8:
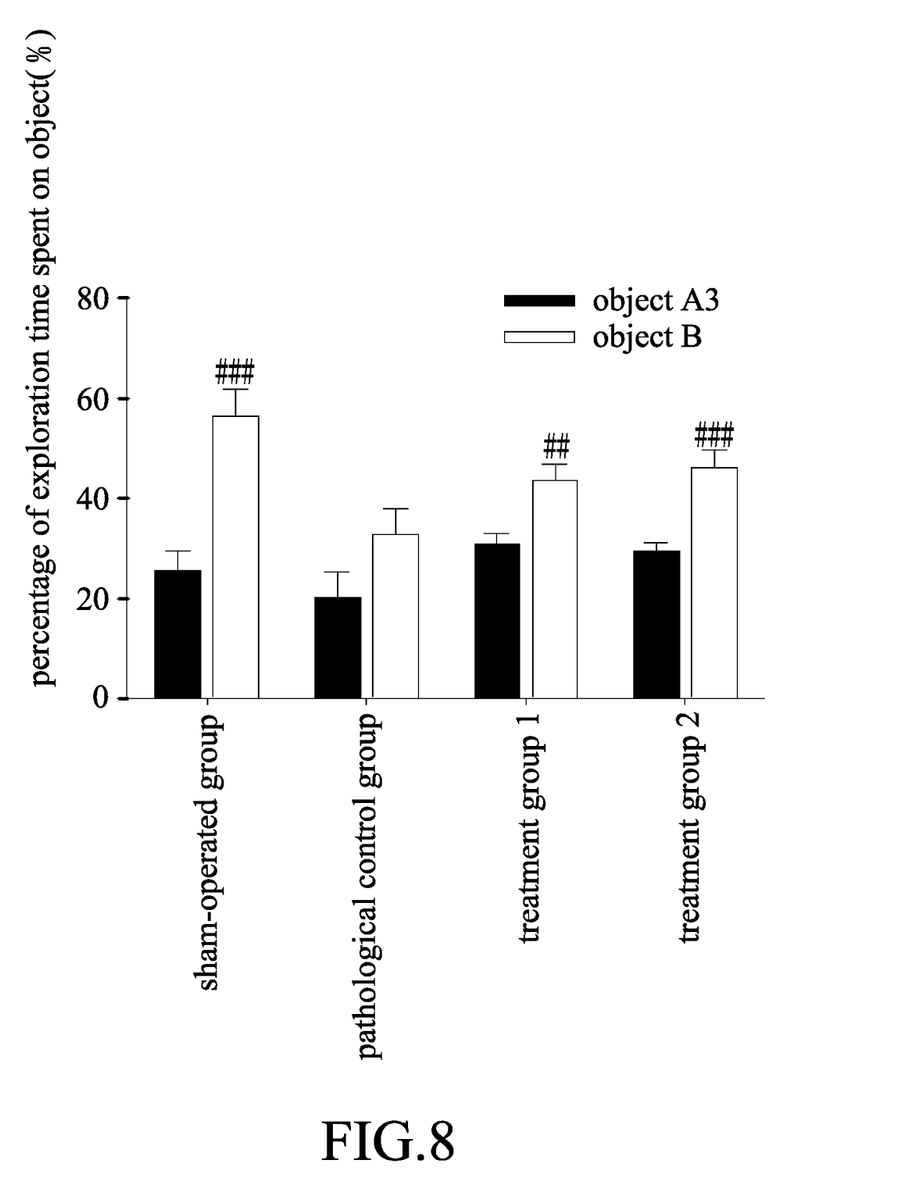
FIG. 8 shows the percentage of exploration time spent on an object A3 in a third trial and the percentage of exploration time spent on an object B in a fourth trial regarding rats in each group as determined via an object recognition test, in which the symbol "##" represents p<0.01 when the percentage of exploration time spent on the object A3 in the third trial and the percentage of exploration time spent on the object B in the fourth trial regarding the respective group are compared; and the symbol "###" represents p<0.001 when the percentage of exploration time spent on the object A3 in the third trial and the percentage of exploration time spent on the object B in the fourth trial regarding the respective group are compared.

FIG. 8 shows the percentage of exploration time spent on the object A3 in the third trial and the percentage of exploration time spent on the object B in the fourth trial regarding the rats in each group as determined via the object recognition test. Specifically speaking, the percentage of exploration time spent on the object A3 in the third trial and the percentage of exploration time spent on the object B in the fourth trial regarding the rats in each group were determined on the 14$^{th}$ day after the MPTP-HCl injection (i.e. the last day of the object recognition test). As shown in FIG. 8, considering the rats in the pathological control group, there is no statistical significance between the percentage of exploration time spent on the object B in the fourth trial and the percentage of exploration time spent on the object A3 in the third trial. On the contrary, considering the rats in the treatment groups 1, 2, there is statistical significance between the percentage of exploration time spent on the object B in the fourth trial and the percentage of exploration time spent on the object A3 in the third trial. The aforementioned experimental results reveal that a low dosage of ceftriaxone is effective in treating PDD, and is able to improve the ability to memorize a familiar object, and the ability to recognize a difference between the familiar object and a novel object, for the rats with PDD.

In view of the results of Examples 1 and 2, it is proven that: considering rats, PDD can be effectively treated and prevented by administering ceftriaxone at a daily dosage ranging from about 10 mg/kg to about 200 mg/kg. The inventor calculated a dosage range suitable for a human subject from the aforesaid dosage range suitable for rats according to the formula for dose translation based on BSA (body surface area), which is described in Shannon R. S. et al. (2007), *FASEB J.*, 22:659-661. Therefore, the inventor deems that a daily dosage of ceftriaxone ranging from about 1.5 mg/kg to about 35 mg/kg is useful in the treatment and/or prevention of PDD in a human subject.

All patents and literature references cited in the present specification as well as the references described therein, are hereby incorporated by reference in their entirety. In case of conflict, the present description, including definitions, will prevail.

While the invention has been described with reference to the above specific embodiments, it is apparent that numerous modifications and variations can be made without departing from the scope and spirit of this invention. It is therefore intended that this invention be limited only as indicated by the appended claims.

What is claimed is:

1. A method for treating Parkinson's disease dementia in a human subject, comprising administering to the human subject ceftriaxone at a daily dosage ranging from about 1.5 mg to about 35 mg per kilogram of a body weight of the human subject.

2. The method as claimed in claim 1, wherein ceftriaxone is administered to the human subject at a daily dosage ranging from about 1.62 mg to about 32.4 mg per kilogram of the body weight of the human subject.

3. The method as claimed in claim 2, wherein ceftriaxone is administered to the human subject at a daily dosage ranging from about 1.62 mg to about 16.2 mg per kilogram of the body weight of the human subject.

4. The method as claimed in claim 3, wherein ceftriaxone is administered to the human subject at a daily dosage ranging from about 1.62 mg to about 8.1 mg per kilogram of the body weight of the human subject.

5. The method as claimed in claim 1, wherein ceftriaxone is parenterally administered to the human subject.

6. The method as claimed in claim 1, wherein ceftriaxone is orally administered to the human subject.

7. A method for treating Parkinson's disease dementia in a human subject, comprising administering to the human subject ceftriaxone at a daily dosage ranging from about 1.5 mg to about 35 mg per kilogram of a body weight of the human subject to ameliorate cognitive functions of the human subject.

* * * * *